(12) United States Patent
Lange et al.

(10) Patent No.: US 11,426,083 B2
(45) Date of Patent: Aug. 30, 2022

(54) EQUIPMENT FOR MONITORING BLOOD FLOW AND RESPIRATORY FLOW

(71) Applicant: IdaHealth, Inc., Kampenhout (BE)

(72) Inventors: Phillippe Lange, Liège (BE); Giovanni Amoroso, Haarlem (NL); David Lawrence Camp, Kampenhout (BE); Gabriele Buttignol, Grevenmacher (LU); Gerrit de Vries, Kampenhout (BE)

(73) Assignee: IDA Health, Inc., Kampenhout (BE)

( * ) Notice: Subject to any disclaimer, the term of this patent is extended or adjusted under 35 U.S.C. 154(b) by 80 days.

(21) Appl. No.: 16/471,823

(22) PCT Filed: Nov. 21, 2017

(86) PCT No.: PCT/EP2017/079918
§ 371 (c)(1),
(2) Date: Jun. 20, 2019

(87) PCT Pub. No.: WO2018/114180
PCT Pub. Date: Jun. 28, 2018

(65) Prior Publication Data
US 2020/0093378 A1     Mar. 26, 2020

(30) Foreign Application Priority Data
Dec. 21, 2016 (BE) .................................. 2016/5953

(51) Int. Cl.
*A61B 5/026* (2006.01)
*A61B 5/0205* (2006.01)
(Continued)

(52) U.S. Cl.
CPC .......... *A61B 5/0205* (2013.01); *A61B 5/0002* (2013.01); *A61B 5/0295* (2013.01);
(Continued)

(58) Field of Classification Search
CPC combination set(s) only.
See application file for complete search history.

(56) References Cited

U.S. PATENT DOCUMENTS 4,258,720 A * 3/1981 Flowers ............... A61B 5/1073
600/500
9,609,921 B1 * 4/2017 Feinstein ............. A44C 5/2071
(Continued)

FOREIGN PATENT DOCUMENTS

| EP | 2581037 A1 | 4/2013 |
|---|---|---|
| WO | 2015172897 A1 | 11/2015 |
| WO | 2018114180 A1 | 6/2018 |

OTHER PUBLICATIONS

International Search Report and Written Opinion dated Feb. 2, 2018, for corresponding International Application No. PCT/EP2017/079918; International Filing Date: Nov. 21, 2017 consisting of 10-pages.
(Continued)

*Primary Examiner* — Nathan J Jenness
*Assistant Examiner* — Skylar Lindsey Christianson
(74) *Attorney, Agent, or Firm* — Christopher & Weisberg, P.A.

(57) ABSTRACT

The subject matter of the invention of the present application is non-invasive equipment for monitoring blood flows and/or respiratory cycles of a human or animal body, comprising at least one segment of conductive elastomer with variable resistance arranged so as to extend over the circumference of the body element and sensitive to the length of the circumference of said element, means for capturing said length by virtue of said variable resistance and supplying a signal representing said length, and means for processing said signal, comprising means for extracting parameters of the blood flows and/or respiratory cycles to be monitored.

13 Claims, 10 Drawing Sheets

(51) Int. Cl.
    *A61B 5/00*      (2006.01)
    *A61B 5/0295*    (2006.01)
    *A61B 5/08*      (2006.01)
(52) U.S. Cl.
    CPC .......... *A61B 5/6833* (2013.01); *A61B 5/0816* (2013.01); *A61B 2562/0261* (2013.01)

(56) References Cited

U.S. PATENT DOCUMENTS

| | | | |
|---|---|---|---|
| 10,076,251 B2 | 9/2018 | Tu et al. | |
| 2008/0300503 A1* | 12/2008 | Lee | A61B 5/002 600/534 |
| 2017/0281082 A1* | 10/2017 | Khine | A61B 5/6824 |
| 2018/0092550 A1* | 4/2018 | Sprenger | A61B 7/04 |
| 2018/0184923 A1 | 7/2018 | Tal et al. | |

OTHER PUBLICATIONS

Xi et al., "Ultrathin and wearable Microtubular Epidermal Sensor for Real-Time Physiological Pulse Monitoring", 2017, Advanced Materials Technologies, vol. 2, p. 1700016; consisting of 8-pages.
Product Data Sheet 3M, Conductive Film Products, 2004, Retrieved from the internet: URL:http://documents.staticcontrol.com/pdf/2004.pdf.
International Search Report and Written Opinion dated Dec. 9, 2020, for corresponding International Application No. PCT/US2020/046068; consisting of 16-pages.
Indian Office Action dated Dec. 3, 2021, for corresponding Indian Patent Application No. 201917026291; consisting of 6-pages.

\* cited by examiner

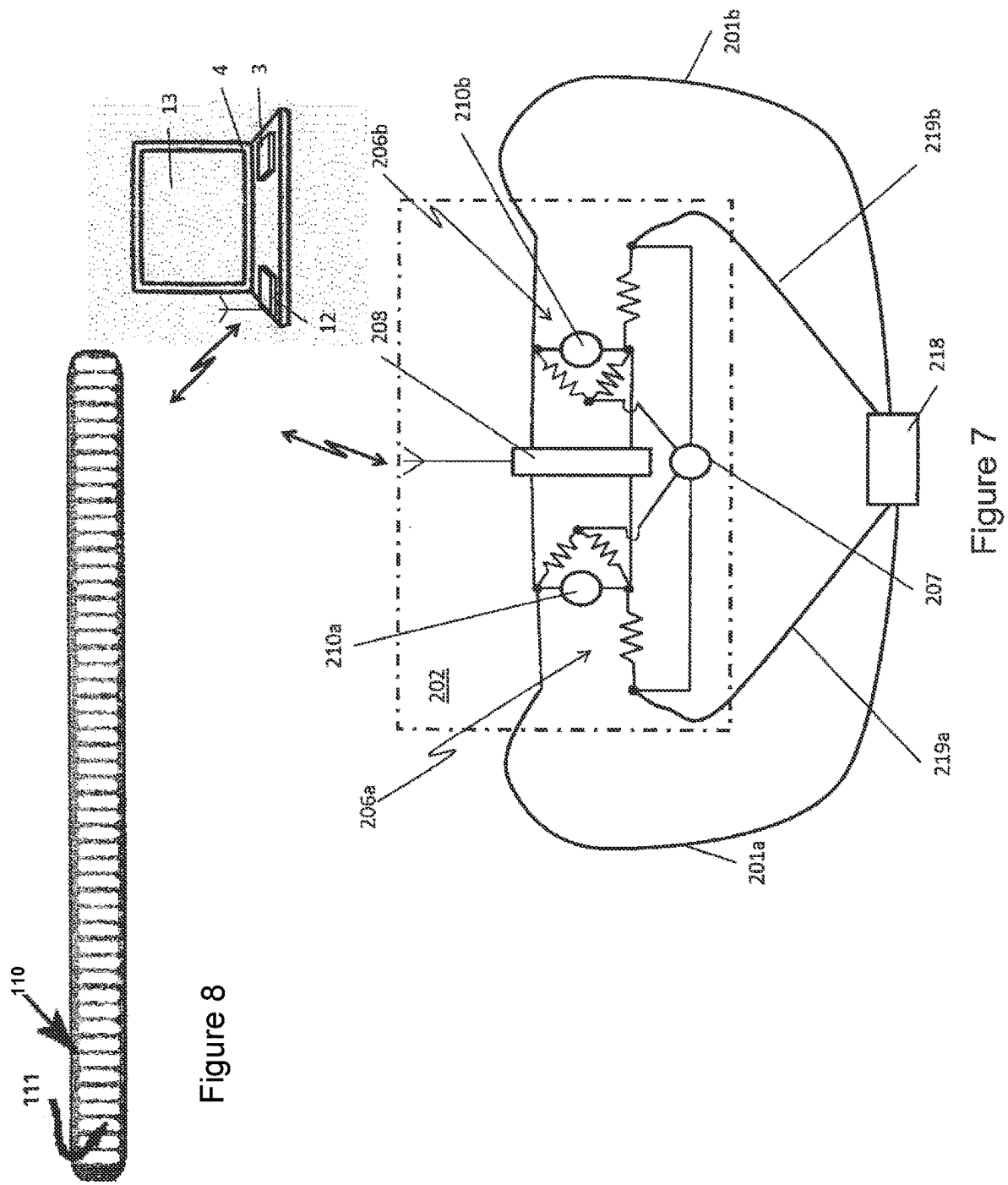

EQUIPMENT FOR MONITORING BLOOD FLOW AND RESPIRATORY FLOW

CROSS-REFERENCE TO RELATED APPLICATIONS

This application is a Submission Under 35 U.S.C. 371 for U.S. National Stage Patent Application of, and claims priority to, International Application Number PCT/EP2017/079918 entitled EQUIPMENT FOR MONITORING BLOOD FLOW AND RESPIRATORY FLOW, filed Nov. 21, 2017, which is related to and claims priority from Belgium Patent Application Number 2016/5953, filed Dec. 21, 2016, the entirety of all of which are incorporated herein by reference.

BACKGROUND OF THE INVENTION

Plethysmography, developed at the start of the twentieth century, makes it possible to measure variations in volume in an organ or the entire body, human or animal, and is, among other things, used to measure peripheral or surface blood flows. In particular, R J Whitney developed, towards the end of the 1940s, a deformation gauge system with a double lead formed by a rubber casing containing mercury (J Physiol, 121, 1-27, 1953). The technology has since been improved. Various techniques are described, using for example a photoelectric sensor illuminating the arteries of the wrist to measure the variation in arterial volume and making it possible to generate an electrical signal that can then be analysed by various methods in order to obtain haematological information. A review of plethysmography methods is available on the internet (http://levelldiagnostics.com/research/P/L1D-PulseWaveMonograph.pdf). However, although very simple and practical to use, the plethysmography techniques currently available suffer from a lack of precision.

The development of the sphygmomanometer, more usually known by the term tensiometer, has led to the gradual abandonment of plethysmography. The tensiometer is based on the principle of a manometer that registers the reaction of the arteries, subjected both to the pressure of the heart and to the pressure of the air produced by the apparatus. Although giving a less precise result over a shorter period than plethysmography, the tensiometer has become adopted for its simplicity of use in doctors' surgeries. It however allows only an approximate evaluation of pressure, representing blood flows, over a short period.

At the same time, electrocardiography has become the examination of choice of the cardiologist for representing the electrical activity of the heart. This examination does however require placing a plurality of electrodes at various places on the body, connected to an analysis unit for monitoring the signals collected.

Doppler echography is also used for exploring intracardiac and intravascular blood flows. The practitioner moves a sensor along the organs to be analysed in order to determine the direction and speed of the blood flow. This examination is however not compatible with prolonged use and requires the active presence of a practitioner.

Cardiovascular ailments are the prime cause of mortality in the world. During the last thirty years, research has made it possible to develop many medicinal treatments against some of the cardiac pathologies. At the same time, surgical techniques have been considerably improved, making it possible in particular to avoid open heart surgery to the maximum possible extent, by favouring for example the installation of arterial support devices, such a stents, arterially, in particular via the radial artery.

Faced with the increase in the number of operations for installing such devices, legislation has allowed an increase in the number of practitioners capable of performing this action, previously reserved solely for the heart surgeon. The increase in the number of such operations has also been accompanied by an increase in the number of post-operative problems.

It turns out that respiratory cycles, that is to say the number of inspirations and expirations per unit of time, also have an effect on blood flows.

In particular, one frequent complication is the post-operative narrowing or even occlusion of the artery (stenosis) by which the medical device was inserted, making a further operation, via the same artery, ineffective or even dangerous. However, it is not rare for the same patient to require several operations of the same type in the course of his life. This problem is described in more detail by Muhammad Rashid et al (J Am Heart Assoc. 2016; doi: 10.1161/JAHA.115.002686). One of the possible causes advanced for explaining this arterial occlusion/stenosis is the compression time and pressure unsuited to the wound resulting from the incision of the artery made at the start of the operation. A correctly carried out compression makes it possible in fact to reduce the risks of occlusion, as described in the article http://www.invasivecardiolgy.com/articles/ulnar-artery-transient-compression-facilitating-radial-artery-patent-hemostasis-ultra-novel. At the present time, no technique is used for monitoring the arterial function in the environment of the wound, neither during the surgical operation nor during the phase of compression of the wound following the intervention, apart from ultrasound monitoring, which is not practical to implement in this context.

There is therefore currently a real lack of a simple, self-contained and compact device that would allow precise monitoring of the arterial function in real time during the surgical operation and, after the operation, during the phase of compression of the wound. This monitoring could enable the practitioner to adapt, in real time, both his operative technique and the pressure exerted on the wound in order to minimise the risks of post-operative problems, such as arterial occlusion.

This is the problem solved by the present invention. The present invention proposes an improvement to plethysmography techniques, advantageously using the advanced technologies in the field of conductive materials.

Heeger, MacDiarmid and Shirawa have shown that non-conductive polymers could be "doped" in order to promote the movement of the electrons along the conjugated double bonds of the polymer and to make this polymer conductive. The document WO 2015/049067 details a method for doping polymers, and in particular elastomers, with nanomaterials, in particular nanomaterials based on carbon, of the graphene type, in order to make these polymers conductive. These conductive elastomers have the property of having a resistance varying as a function of their length, that is to say the stress that is applied thereto. This is detailed in the above patent document, which suggests the use of this property for measuring subtle physiological movements such as the pulse or respiration.

The present invention relates to non-invasive plethysmographic equipment including a conductive elastomer with variable resistance that can be used in particular in the operating theatre, not causing any problem for the practitioner or practitioners.

SOLUTION OF THE INVENTION

Thus the subject matter of the invention of the present application is first of all a non-invasive equipment for monitoring blood flows of a body element comprising a network of channels through which said blood flows travel, comprising:
- at least one segment of conductive elastomer with variable resistance arranged so as to extend over the periphery of the body element and sensitive to the length of the periphery of said element,
- means for capturing said length by virtue of said variable resistance and supplying a signal representing said length, and
- means for processing said signal, comprising means for extracting parameters of the blood flows to be monitored.

The subject matter of the invention of the present application is also non-invasive equipment for monitoring respiratory cycles of a human or animal body causing a variation in the length of the periphery of a body element, comprising:
- at least one segment of conductive elastomer with variable resistance arranged so as to extend along the periphery of the body element and sensitive to the length of the periphery of said element,
- means for capturing said length by virtue of said variable resistance and supplying a signal representing said length, and
- means for processing said signal, comprising means for extracting parameters of the respiratory cycles to be monitored.

The applicant is therefore started from document WO 2015/049067 for solving the problem presented above. This document does not however describe the application of conductive elastomers with variable resistance to plethysmography equipment and is therefore excluded legally from the field of the prior art. A person skilled in the art reading this document, in particular the paragraph relating to sensors (page 24, lines 24-33), faced with the broad field of the possibilities of use of such sensors, could not be guided to the particular implementation of plethysmography equipment using conductive elastomers with variable resistance.

Blood flows correspond to the flow of the blood in blood vessels and the heart. Blood vessels are all the conduits that convey the blood and comprise arteries, veins, venules and capillaries.

Non-invasive monitoring equipment is equipment that makes it possible to monitor one or more parameters, not requiring any infraction to the skin. It is generally accepted that a simple taking of blood and an injection of product are also of a non-invasive nature. The non-invasive character of an item of equipment generally involves an absence of danger.

In a preferred embodiment, the segment of conductive elastomer with variable resistance is arranged to surround the body element and is sensitive to the length of the periphery of said element.

In another advantageous embodiment, the segment of conductive elastomer with variable resistance is secured to an adhesive piece.

In any case, the conductive elastomer is, obviously, placed in direct contact with the skin. Placing the elastomer on a fabric covering the skin, such as an item of clothing, would reduce the sensitivity of the device significantly.

Body element means here any part of the body able to be covered or surrounded, in whole or in part, by the elastomer segment. These body elements may comprise the lungs, the trunk or the throat. They may belong to a human or to an animal.

The periphery of the body element refers to a line that forms the limit of the surface of this element. The elastomer segment may for example extend over a part of the trunk or of the neck. The length of the periphery may be only a fraction of the length of the periphery of the body element. In addition, "surrounding the limb" does not necessarily mean that the segment is closed on itself around the limb, since the capturing means and processing means are disposed around the limb. The terms "turn" and "periphery" will be used indifferently in the remainder of this document.

An adhesive piece designates here a thin layer of a polymer tissue or any other suitable material, covered, on at least one of its faces, with an adhesive or sticky substance that enables the piece to adhere durably to the skin, at the body element where it is placed. Such adhesive pieces are in particular used in dressings or in what is commonly referred to as a patch.

In the preferred embodiment of the invention, the means for capturing said length comprise at least one measuring bridge, of which at least one of the resistances is formed by the conductive elastomer with variable resistance. The electrical signal output from the measuring bridge is an image of said length of the periphery.

A measuring bridge designates here an electronic assembly comprising at least one resistance, the value of which varies according to a parameter to be measured, here a length. A well-known example of a measuring bridge is the Wheatstone bridge, but there also exist numerous variants such as alternating-current bridges, Owen bridges, Schering bridges and Robinson bridges which make it possible to improve the measurement precision.

The variation in length of the conductive elastomer, that is to say the variation in the length of the periphery of the body member to be monitored, causes a variation in the resistance of the conductive elastomer, which is assessed by means of the measuring bridge and is an image of the blood flows at the member around which the conductive elastomer is placed. The principle of the Wheatstone bridge is well known to persons skilled in the art. Its application to deformation gauges is widely documented (*What's The Difference Between Operational Amplifiers And Instrumentation Amplifiers, Electronic Design*, 26 Aug. 2015; *Signal Conditioning Wheatstone Resistive Bridge Sensors, Texas Instruments, Application Report SLOA034*, September 1999). As a general rule, the measuring bridge carries out herein the function of electronic amplifier, and may be an operational, differential or instrumentation amplifier. The measuring bridge may also be referred to as a measuring circuit, the bridge concept being linked with the presence of the variable-resistance conductive elastomer.

In an advantageous embodiment of the invention, the processing means are electronic means and the means for extracting parameters of the blood flows to be monitored comprise an algorithm arranged to receive the information relating to said length in order to extract therefrom the parameters of the blood flows to be monitored.

Such algorithms are described in BioMedical Engineering OnLine, 20054:48 (DOI: 10.1186/1475-925X-4-48). They make it possible in particular to separate the information relating to the arterial flows from the information relating to the venous modes and/or to the respiratory cycles. They also make it possible to analyse the relationships between these two flows.

The invention will be understood better by means of the following description of several embodiments of the invention, with reference to the accompanying drawing, on which:

FIG. 7 is a view of the equipment in FIG. 7 with, in detail, the capture and processing box;

FIG. 8 shows a form of a segment of conductive elastomer;

Figure 1:
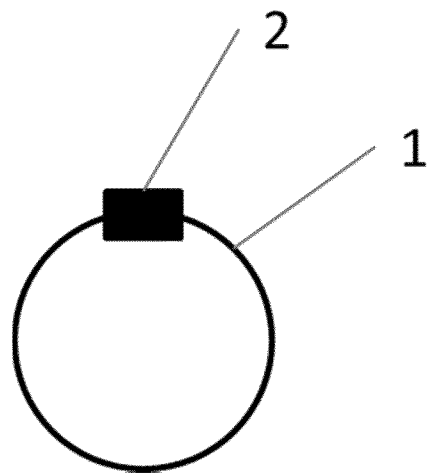
FIG. 1 shows a schematic view of the equipment for monitoring blood flows according to the invention.
Figure 2:
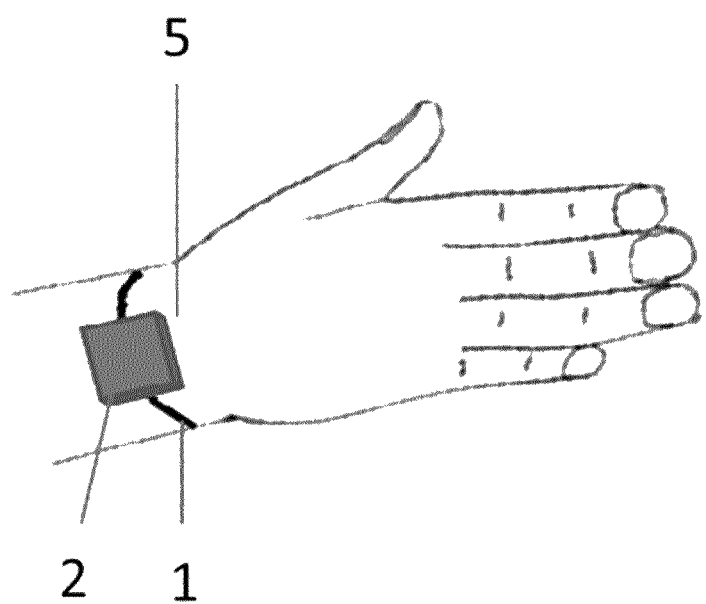
FIG. 2 shows the equipment in FIG. 1 around the wrist of a patient.
Figure 3:
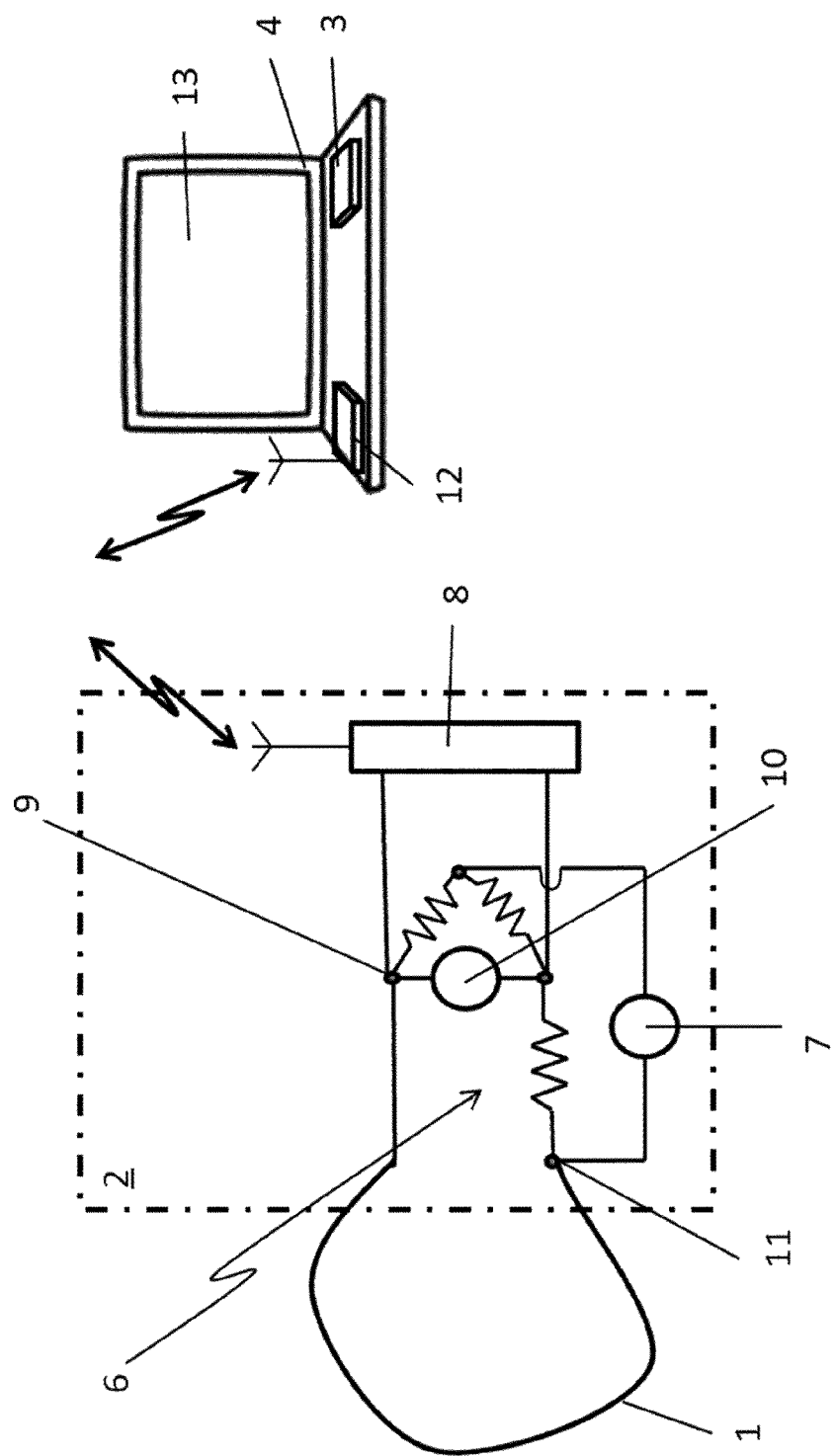
FIG. 3 is a view of the equipment in FIG. 1 with, in detail, the capture and processing box.

With reference to FIGS. 1 to 3, the plethysmographic equipment of the invention comprises a bracelet 1 for holding a box 2 for capturing and processing signals and, here, housed in the data processing system 4, an algorithm 3, the function of which is combined with those of the processing means of the box 2.

The bracelet 1 is here a segment of elastomer intended to partly surround here a wrist 5 and fixed to the box 2 in order to hold the latter on the wrist 5. The elastomer segment and the box can be connected in a simple standard fashion, for example by means of an adhesive tape under the protected trade mark "Velcro®" or in the manner of a watch bracelet holding the watch casing. The bracelet 1 is made from conductive polymer intended to be pressed against the skin of the wrist 5.

The box 2 contains a Wheatstone bridge 6 supplied by a power source 7 and connected at its output to a wireless transmitter 8. The bracelet 1 is integrated in the bridge 6 as an unknown resistance to be assessed, and connected at one 9 of the two ends of the diagonal of the bridge 6 wherein there is disposed a detector 10 that is connected to the transmitter 8 and at one 11 of the two ends of the other diagonal of the bridge 6 connected to the power source 7.

The data processing system 4 wherein the algorithm 3 is loaded comprises a receiver 12 arranged so as to be connected to the transmitter 8 of the box 2. The algorithm 3 therefore cooperates with the measuring bridge 6, the wireless transmitter 8 and the wireless receiver 12.

As a power source 7, an electric cell or a rechargeable battery can be envisaged.

The connection between the transmitter 8 and receiver 12 may be a Bluetooth or WiFi connection or any other wireless technology.

As a data processing system, a computer, a touch tablet, a smartphone or even a connected watch can be considered.

The correct positioning and adjustment of the tension of the conductive elastomer are important so as to have a signal of optimum quality. The length of the elastomer may be adjusted so that the tension of the conductive elastomer is sufficient for the detection of its variations in length, and therefore resistance, but not too great, so that the blood circulation is not affected. The length of the bracelet 1 can be adjusted to the periphery of the wrist manually or automatically.

The structural features of the equipment of the invention having been described, its functioning will now be dealt with.

During its functioning, the length of the conductive elastomer varies according to the venous flow, the arterial flow and the respiratory volume. The Wheatstone bridge 6 comprising the bracelet 1 made from conductive elastomer will generate an electrical signal that is the image of these physiological parameters. This signal can then be amplified before being transmitted by the transmitter 8 to the receiver 12 of the data processing system 4 comprising the algorithm 3, making it possible to extract from the signal received its various components.

The algorithm 3 can in particular make it possible to isolate the electrical signal relating to the arterial pulse and the electrical signal relating to the venous flow. It can also make it possible to analyse the difference between these two flows as well as the first or second derivatives of the difference between these two flows. It may further also comprise a frequency analysis in order to separate the flows more clearly, for better signal quality. This information may then be displayed on the screen 13 of the data processing system 4.

The information displayed may be diverse and suited to the context of use of the equipment of the invention. Typically, the change in the physiological parameters, or their relationship to each other, calculated by the algorithm 3, as a function of time, will be displayed in a way that is simple for the practitioner to analyse.

During a surgical operation aimed at introducing a device of the stent type, for example through the radial artery, an incision in the radial artery is made at the forearm. It can then be envisaged positioning the bracelet 1 between the hand and the incision. This is made possible by the small size of the bracelet 1, which is not bulky and does not comprise any electrical connections that could interfere with the work of the practitioner. The practitioner can then, in real time, during the introduction of the stent, monitor the arterial and venous flows at the wrist and adapt his operation accordingly. Likewise, at the end of the operation, a practitioner will apply pressure at the wound resulting from the incision of the artery, in order to stop the bleeding. By being capable of monitoring the arterial and venous flows in real time, the practitioner will be able to adapt the pressure applied to the wound.

Figure 15:
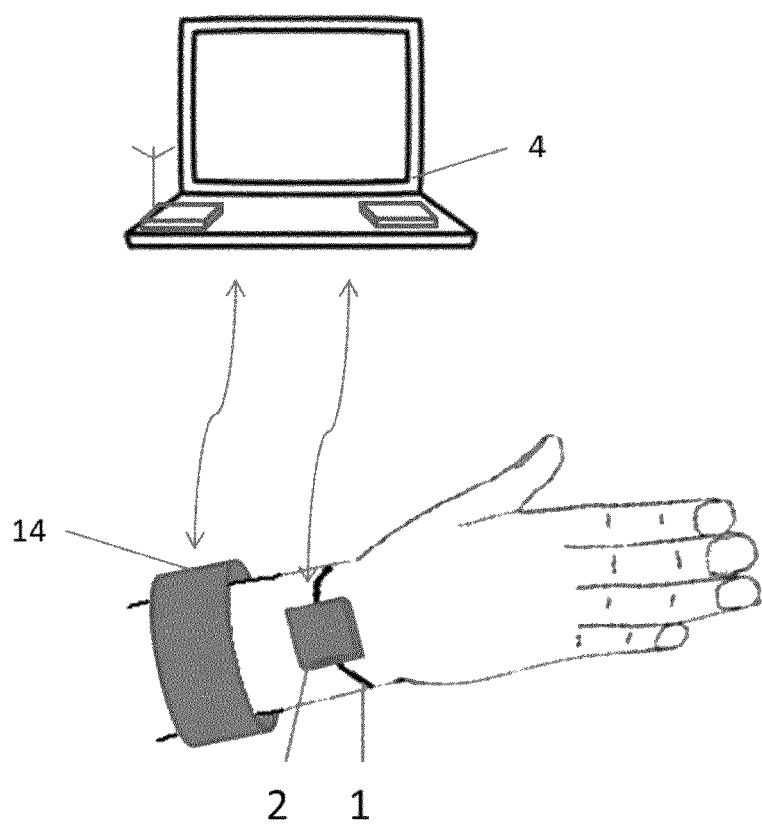
FIG. 15 illustrates the equipment of the invention associated with an automatic compression bracelet.

In the case, illustrated in FIG. 15, wherein this wound compression phase would be managed by an automatic wound compression device 14, such as for example that presented by Terumo TR Band® (http://www.medicalexpo.fr/prod/terumo-medical/product-71204-45828.html), it may be envisaged that the pressure applied by the automatic compression device be controlled, wirelessly, by an additional algorithm integrated in the data processing system 4 as a function of the analysis of the data supplied by the bracelet 1. The medical compression device may be connected wirelessly to the data processing system or, depending on the circumstances, via a direct wired connection to the bracelet box. Different types of compression may be applied and controlled via the measuring device, connected directly and/or wirelessly. The compression may for example be carried out by pressure from an external element, such as for example a hard or soft sphere, an air chamber or a chamber containing an optionally compressible fluid.

The correct positioning and adjustment of the tension of the elastomer segment 1 are important for the quality of the signal measured and consequently the quality of the parameters extracted by the detection and analysis algorithms. The operator easily positions a bracelet on the wrist, close to the hand, but in a position not interfering with the surgical operation. The tricky adjustment then consists mainly of tightening the bracelet in order to adjust its pressure or tension. This is managed by adjusting the length of the conductive elastomer tape to an optimum force or tension at which the elastomer remains sufficiently flexible but not too slack. It is important to note that the absolute force on the elastomer affects not the measurement but its precision. This is related to the physical characteristics of elastomer such as for example its modulus of elasticity, its temperature and its dimensions. The elastomer may be manufactured in a specific form so that it is more flexible, which means that it will give greater precision and its length will be easier to adjust.

The adjustment of the length of the elastomer may advantageously be facilitated by the use of a locking system cooperating with the segment of conductive elastomer. In order to facilitate this cooperation, the conductive elastomer tape 1 may consist of a continuous material 110 having a particular relief, such as for example a repetitive relief 111 as illustrated in FIG. 8. The relief is here a perforation having the form of a rectangle with rounded corners, but it may adopt any form compatible with the strength, precision, flexibility and resistance required for the bracelet 1. The relief may, for example, be a jamming pattern as used for example on a clamping collar. This embodiment also improves the electrical contact between the conductive elastomer and the mechanical part connected to the electronic parts of the box 2.

In the same way, the adjustment of the bracelet 1, at the time when it is installed on the wrist, may also be controlled by yet another algorithm integrated in the data processing system 4, according to the analysis of the data supplied by the bracelet 1, a drive member making it possible to tighten the conductive elastomer to its optimum tension for monitoring.

Figures 9A, 9B:
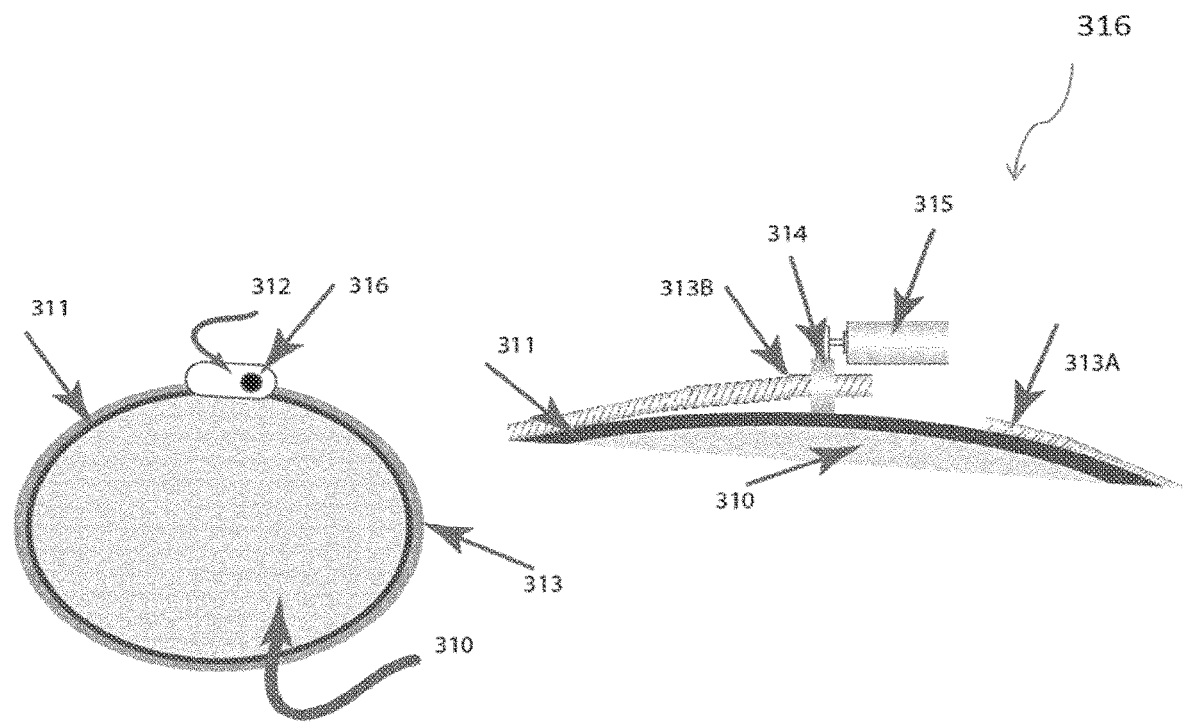
FIGS. 9a and 9b show another embodiment of the equipment for monitoring blood flows, comprising a system for adjusting the length of the variable elastomer segment.

With reference to FIGS. 9a and 9b, the skin 311 of the wrist 310 is surrounded by the segment of conductive elastomer 313 and a box 312 containing the electronic elements of the equipment as well as a clamping member 316. The clamping member 316 comprises a motor 315 which, by means of a clamping ring 314, allows a movement of the segment of conductive elastomer at its end 313B, thus adjusting its length, the other end 313B being fixed to the box 312. The motor 315 may be controlled by the data processing system 4, and will cause the tightening or slackening of the elastomer segment 313 to its optimum tension. This tension is proportional to the resistance of the elastomer and can be extracted from the electrical signal generated by the device. It can be envisaged that the end of the adjustment operation may be signalled to the operator, for example by means of a visible light signal on the box 2, a message on the screen 13 of the data processing system 4, an audible signal emitted at the box 2 or data processing system 4, a vibration of an element of the device or a combination of a plurality of these signals.

One advantageous application of the invention is the simultaneous use of a plurality of bracelets 1. A second bracelet may be placed between the elbow and the shoulder in order to generate a second electronic signal that can be analysed in relation to the first electrical signal and give the practitioner additional information relating to the blood flows at the arm overall. In a similar fashion, one or more bracelets may be disposed symmetrically on the second arm in order to obtain a so-called "reference" signal with respect to which the blood flows of the arm undergoing the operation can be compared.

Figure 4:
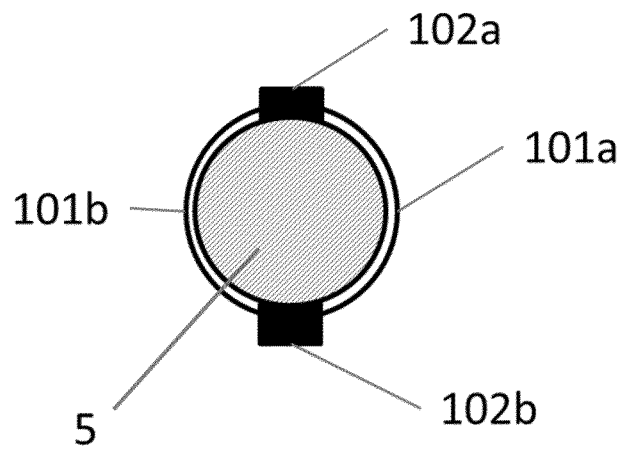
FIG. 4 shows another embodiment of the equipment for monitoring blood flows, comprising segments of conductive elastomer and positioned around the wrist of a patient.
Figure 5:
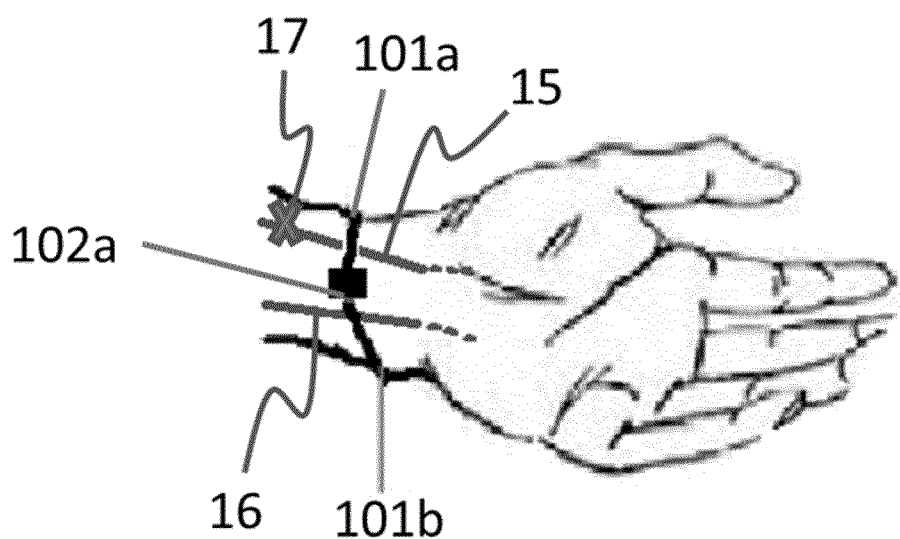
FIG. 5 illustrates the arrangement of the equipment in FIG. 5 on the inside of the wrist, with respect to the arteries of the wrist and to an incision made on the radial artery.

With reference to FIGS. 4 and 5, the non-invasive plethysmographic monitoring equipment of the invention may comprise two segments of a conductive elastomer arranged to surround the body member.

Two segments of conductive elastomer 101a and 101b are each connected by one end to a box 102a and by their other end to a box 102b and partly surround the wrist 5. The two boxes 102a and 102b each consist in a similar fashion of the previously described equipment. When the bracelet is fitted, the first box 102a is placed between the radial artery 15 and the ulnar artery 16, and the second box 102b is placed on the top of the wrist. In this configuration, the variation in the length of the segment of conductive elastomer 101a relates to the radial artery 15 and the variation in the length of the segment of conductive elastomer 101b relates to the ulnar artery 16. This configuration makes it possible to obtain two separate electrical signals that can be transmitted by the wireless communication units of the boxes 102a and 102b to the data processing unit 4 comprising the algorithm 3 capable of processing these signals in order to extract the blood-flow parameters therefrom, which enables the practitioner to obtain more precise information relating to each artery separately. In particular, if he makes an incision 17 on the radial artery, he can compare the blood flows in the two arteries on the wrist and adapt his operation if required. A Wheatstone bridge type circuit was used here, but it is obvious that any suitable analogue system, well known to those skilled in the art, making it possible to convert the length information of the elastomer segment into electrical current and/or into digital information can also be envisaged, such as for example other forms of measuring bridges or amplifier, in particular a differential amplifier.

Figure 6:
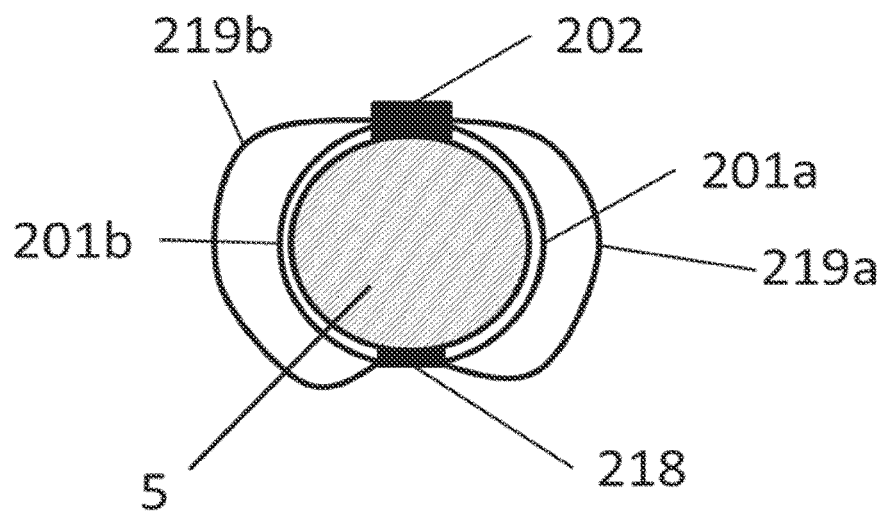
FIG. 6 shows another embodiment of the equipment for monitoring blood flows, comprising two segments of conductive elastomer and positioned around the wrist of a patient.

With reference to FIGS. 6 and 7, an alternative variant analysing separately the signals relating to the ulnar 16 and radial 17 arteries is using two segments of conductive elastomer 201a and 201b. These are each connected by one end to a box 202 and by their other end to a fixing element 218 and partly surround the wrist 5. In this case, the box 202 comprises two Wheatstone bridges 206a and 206b each including one of the two elastomer segments 201a and 201b as an unknown resistance. Since each end of the elastomer must be connected to the Wheatstone bridge for correct functioning, it is necessary to add two conductive wires 219a and 219b completing the loop formed respectively by the elastomer segments 201a and 201b in their respective Wheatstone bridge. These Wheatstone bridges are each connected to a detector, respectively 210a and 210b, and are both connected to a transmitter 208 and a power source 207.

A similar configuration can be envisaged with three elastomer segments or more, each segment being included in a measuring bridge, but all being connected to the same transmitter.

Likewise, the use of the equipment of the invention is not limited to the wrist or arm; it can also be used on other members or organs according to the requirements of the practitioner; for example when fitting a stent is done via the femoral artery, the bracelet can be placed at the thigh.

The use of the invention is not limited to uses during surgical operations. It can apply to any other activity of monitoring blood flows and/or respiratory cycles.

One example is the monitoring of sleep apnoea. The patient can then be equipped with equipment of the invention, in the form of a bracelet or patch, connected during his sleep to an analysis periphery such as his smartphone, which contains an application analysing the signal transmitted by the electronic device of the equipment and which can emit an audible and/or light signal intended to wake the patient if the apnoea becomes dangerous for him.

The equipment for monitoring blood flows and/or respiratory cycles, comprising one or more segments of conductive elastomer, can be used on numerous parts of the body. It can be used ante, per or post-surgical operation. It can also be used in the longer term, for days, weeks or months, to monitor physiological parameters of a patient, such as for example the arterial and/or venous flows and his cardiac coherence.

Figure 10:
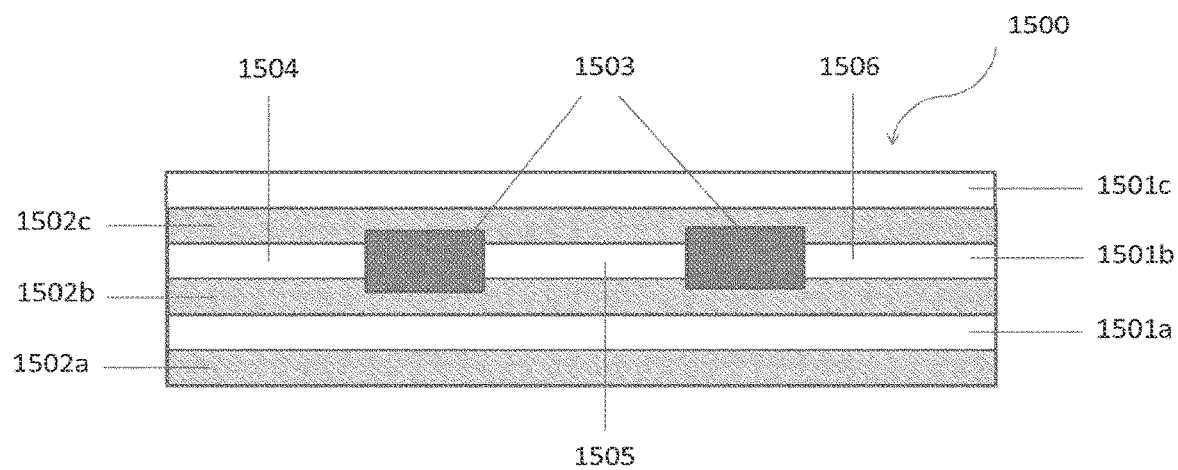
FIG. 10 shows a particular configuration of the segment of conductive elastomer.
Figure 11:
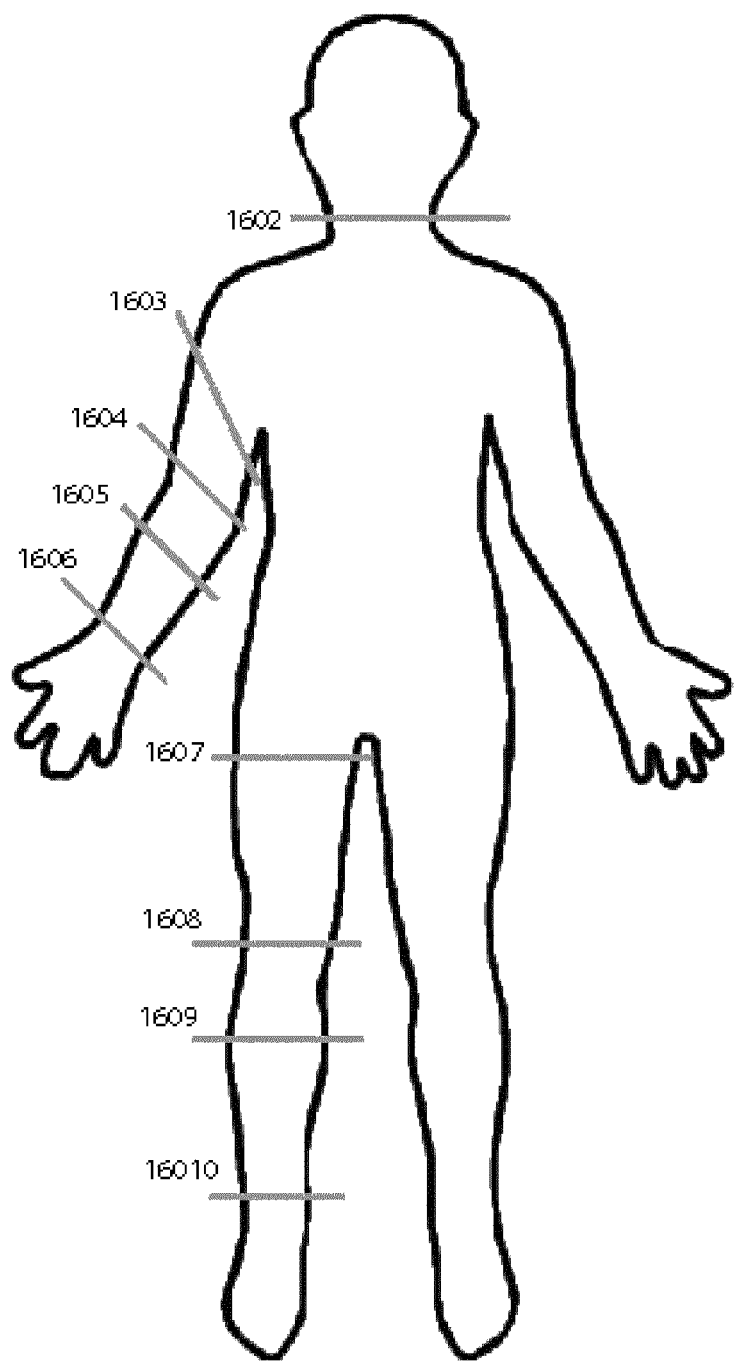
FIG. 11 illustrates the possible uses of the equipment of the invention.

With reference to FIG. 10, the equipment of the invention can be used at the wrist 1606, the ankle 1610 or the knee 1609 to monitor venous problems in the leg, at the top of the thigh 1607 to monitor the femoral artery, or at the lower part of the thigh 1608 to detect arterial and/or venous occlusions. It can also be applied to various levels of the upper arms 1603 and 1604 and/or of the forearms 1605 and 1606 to detect arterial and/or venous occlusions. It can also advantageously be used to monitor the physiological behaviour of the penis in order to clarify the type of erectile dysfunction.

An application of the device at the neck 1602 makes it possible to monitor the respiratory rhythm, instabilities in the respiratory cycles and the arterial and/or venous flows to the brain.

The monitoring segment of conductive elastomer can also be installed at the trunk, for example around the waist 1627, to monitor the movements of the abdomen, for example to monitor the behaviour of the abdominal wall after an intestinal operation, or at the chest 1626 to monitor the respiratory cycle, cardiac coherence and the arterial and/or venous cardiac activities.

Secondarily, the device of the invention can be arranged aesthetically, as a kind of jewel, in order to be able to be used during the day and night in an elegant, practical and comfortable manner.

Another very useful and novel embodiment of the invention is to connect the segment or segments or conductive elastomer and the capture and/or processing means to an adhesive part in order to form a device of the patch type.

Figure 12:
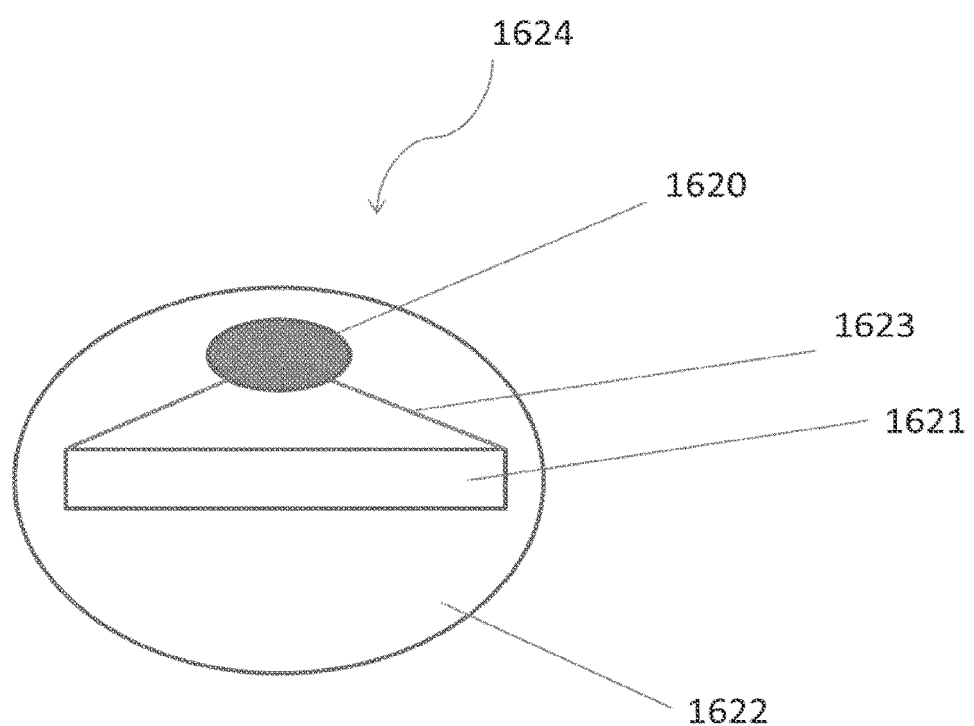
FIG. 12 shows the equipment of the invention integrated in an adhesive piece.

With reference to FIG. 12, a segment of conductive elastomer 1621 is connected to a capture device 1620 by electrical connectors 1623. The elastomer 1621 and the capture device 1620 are disposed on the sticky face of an adhesive part 1622, the whole forming a patch 1624. The capture device 1620 comprises the same elements as the boxes 2 and 202 already described. This patch 1624 can be used for example on the chest or on the abdomen to measure cardiac coherence, the respiratory rate and blood circulation. In particular, this patch can serve to assess whether the respiration of a patient is deep or only on the top part of the lungs (incoherence), which is an indication of the sympathetic or parasympathetic equilibrium of his metabolism. The patch 1624 can also be used for measuring the function of the bladder, which is a very important parameter when a patient is in intensive care.

It is possible to manufacture the segment of conductive elastomer of the invention "in layers" in order to reduce the size, the production cost and the weight and to simultaneously increase its sensitivity and measuring precision. This multilayer construction consists of an alternation of layers of the conductive elastomer with layers of non-conductive elastomer. This advantageous construction makes it possible to carry out a plurality of measurements using only one stratified segment 1500.

With reference to FIG. 10, the elastomer segment 1500 here consists in alternation of layers of conductive elastomer 1501 (a, b and c) and layers of non-conductive elastomer 1502 (a, b and c), which may have identical or different rigidity values. The layers of conductive elastomer 1501a, b and c may also have conductivity values different from one another. These layers 1501a, b and c are connected to the rest of the device by electrical connectors. A layer of non-conductive elastomer 1502a advantageously forms the external layer intended to be in contact with the skin of the patient, in order to isolate the device electrically.

In one embodiment, all the conductive layers cover the entire length of the segment 1500.

It can also be envisaged that a part of the conductive layer, here the layer 1501b, may be "divided", that is to say interspersed over its length with non-conductive sections 1503 in order to form conductive sections 1504, 1505 and 1506. Each conductive segment is connected to the rest of the device by judiciously arranged electrical connectors. This division confers on the layer 1501b the properties previously described for bracelets consisting of a plurality of segments of conductive elastomers, and makes it possible to isolate signals coming from different venous or arterial flows, such as for example the flows relating to the ulnar artery and to the radial artery.

The non-conductive sections 1503 may be made from elastomer or not, and optionally manufactured from different materials.

The segment 1500 may comprise a plurality of identical conductive layers each generating a signal that can be treated separately or statistically or by calculating the interactions of the signals from similar layers.

In general, the electrical connections may be produced from any suitable material, for example both metals, such as copper, and conductive inks.

An elastomer segment, comprising a layer or a superimposition of a plurality of layers, may be used to design equipment designed for specific monitoring. For example, an elastomer segment designed for monitoring the femoral artery may have the same construction as a segment of elastomer designed for monitoring the radial artery at the wrist, but will be adapted in its dimensions according to the use.

The means for extracting the parameters of the blood and/or respiratory flows to be monitored comprise an algorithm using a certain number of steps to convert the signal measured at the measuring bridge into a signal that can be viewed by an operator.

Figure 13:
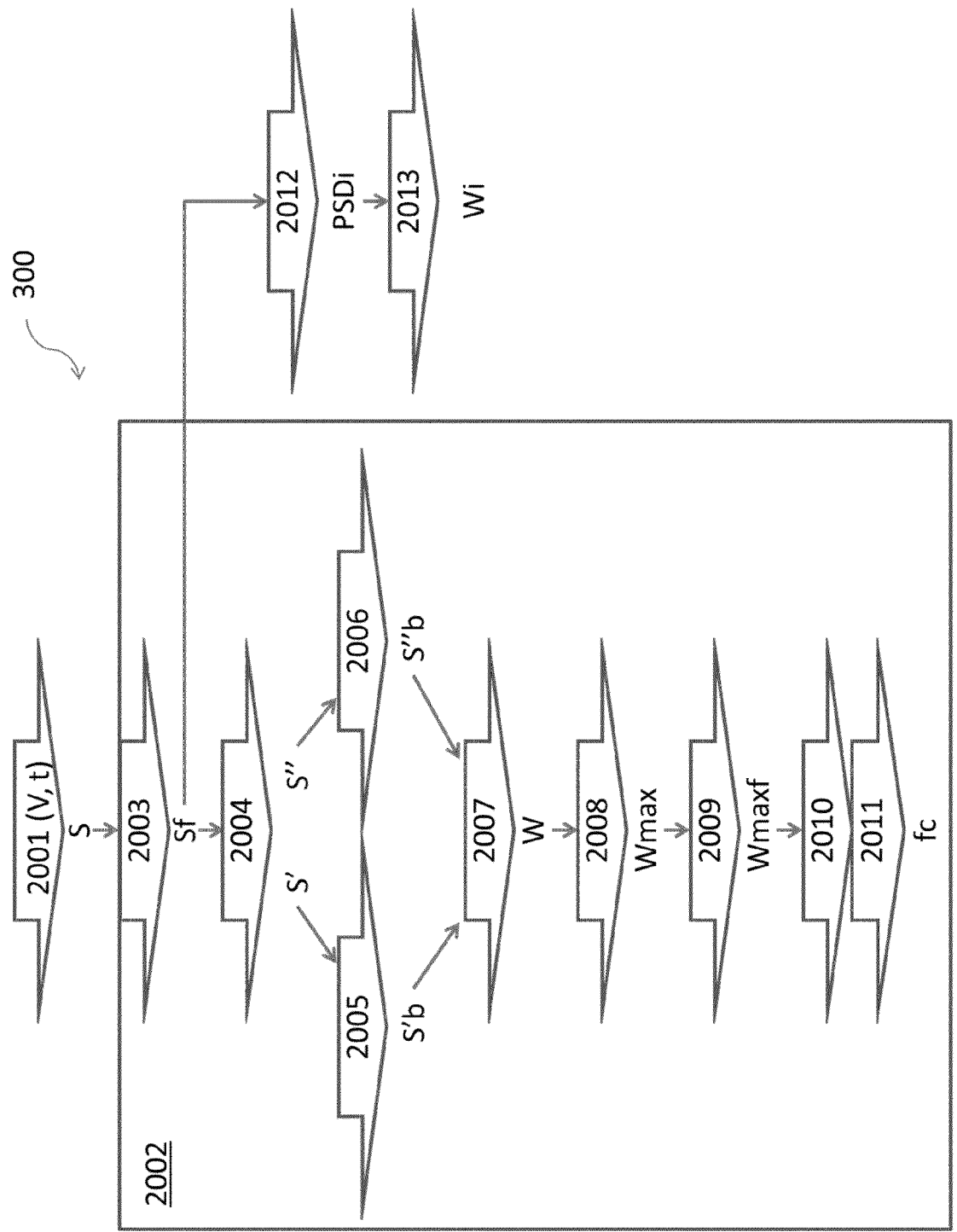
FIG. 13 illustrates an algorithm of the equipment of the invention.

With reference to FIG. 13, in a first step 2001, an electrical signal s, here a voltage v, is measured over a time t for each elastomer segment. The electrical signal comprises voltage maxima and minima, from which the mean cardiac frequency fc is extracted. For example, for a human, the cardiac frequency is between 0.25 and 4 hertz. For a correct measurement, a sampling frequency, that is to say the frequency at which the extraction of the cardiac frequency can be done, of 200 Hz is sufficient. In practice, the extraction 2002 of the cardiac frequency fc comprises a plurality of steps 2003 to 2011.

In a first step 2003, the signal S passes through a bandpass filter, that is to say one allowing to pass only a band or range of frequencies lying between a low cutoff frequency and a high cutoff frequency of the filter, such as for example a filter of the FIR (finite impulse response) type. From the resulting signal Sf, in a second step 2004, the first S' and second S" derivatives are extracted. In digital mode, the first and second derivatives are calculated conventionally by S' (n)=S (n+1)−S(n) and S" (n)=S'(n+1)−S'(n) where n is the number of the sample.

At step 2005, the first derivatives S' are binarised into signals S'b, replacing the positive values of the signals S' by 1 and the negatives by 0. In an independent and/or parallel step 2006, the second derivatives are rectified into signals S"p by setting all the negative values to 0.

In a calculation step 2007, the product of the binarised first derivatives S'b and the rectified second derivatives S"p gives the signal W, from which it is possible, at step 2008, to identify the maxima Wmax. Applying a so-called "weight" digital filter, at step 2009, makes it possible to extract from these maxima Wmax the component Wmaxf relating to the arterial frequency. The signal Wmaxf is next once again processed in order to eliminate the "noise" therefrom, by a bandpass filtering 2010.

It is then possible to detect the interval of time between two maxima of an arterial pulsation signal in order to extract the cardiac frequency therefrom at step 2011.

The cardiac coherence, that is to say the variation in the cardiac frequency, as defined by the Heartmath Institute, can be deduced therefrom.

Cardiac coherence is a monitoring that analyses the heartbeat rate compared to the previous beat. This process is at the source of the equilibrium of the sympathetic and parasympathetic systems of the body. This monitoring can make it possible to evaluate in particular a subject's stress level and optionally detect the onset of conditions such as burnout, depression, or stroke.

In the case where the equipment comprises a plurality of elastomer segments, the signals corresponding to each segment are processed separately and each undergo all the steps 2003 to 2011.

The other parameters of the blood flows and respiratory cycles can also be extracted, from the same signal Sf issuing from the bandpass filtering step 2003.

In a step 2012, for each elastomer segment, the signal Sf is processed by vibratory analysis integrating a fast Fourier transformation (FFT), from which the spectral power density PSDi for each frequency group is extracted, that is to say on frequency bands each corresponding to a separate physiological parameter, such as for example the frequencies of the venous system and of the arterial system and the respiratory frequencies. Each physiological function may in fact be associated with a set of frequencies that make it possible to characterise it in its cycle, its energy and its dynamics. The signals PDSi obtained for each frequency band can then also be weighted by their energy and intensity, in a step 2013, in order to generate signals Wi representing each physiological function measured, for example a respiratory signal Wr, a venous signal Wv or an arterial signal Wa.

The frequency bands considered, for each elastomer segment, may depend on the specific placement of the segment on the body element and the dominant signals expected for these locations.

In the case where the equipment comprises a plurality of elastomer segments, the signals Wi obtained for each segment can be compared in order to facilitate the automatic detection of the types of physiological parameters mainly detected by each elastomer segment.

All the steps of the algorithm 300 described above are generated in real time by the data processing system, and the signals that result therefrom can be viewed by an operator.

During the performance of the steps of the algorithm 300, all the measured values, the signals or the calculation results can be saved in non-volatile memories, local or remote, such as for example hard disks or the Cloud.

The steps of the algorithm 300 are detailed here by way of example. The nature, the number and the sequencing of the steps may obviously be different in order to construct an algorithm making it possible to extract, from the measurement of the length of the variable elastomer segment, any information that can be used by a practitioner.

Figure 14:
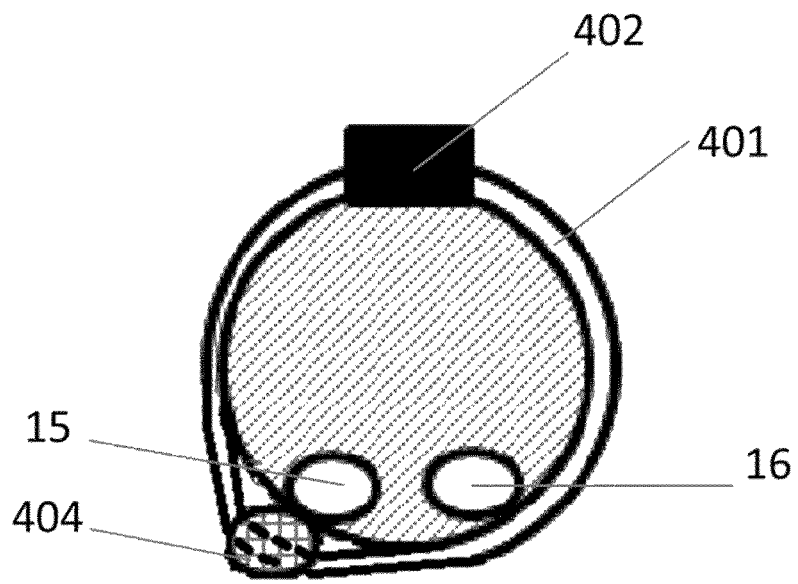
FIG. 14 illustrates the equipment of the invention comprising an extension member of a conductive elastomer of the equipment according to the invention.

With reference to FIG. 14, the applicant was surprised to observe that inserting an extension member of the static length of the segment of elastomer, herein a bead 404, positioned between a segment of conductive elastomer 401 connected to a box 402 and the periphery of the wrist 5, specifically at the level of the radial artery 15, makes it possible to enhance the precision of the signal measured related to this radial artery 15 significantly.

Indeed, the presence of the bead makes it possible, by a geometric effect, by separating the elastomer segment 402 slightly from the arm 5, to amplify the variation in length due to the variation in diameter of the radial artery, i.e. amplify the amplitude of the signal by increasing the sensitivity thereof.

A bead is used herein. The latter being slipped onto the elastomer segment, it is readily movable therein by sliding and is not liable to be detached therefrom. However, any other positionable rigid element, i.e. suitable for being stably positioned over time in a specific location of the body member, for example at the level of the artery to be monitored, between the skin and the elastomer, may be envisaged. The element may for example have a cubic, hemispherical shape or any other shape deemed suitable by those skilled in the art. The rigid element may be manufactured with any suitable material, and may for example be made of wood or plastic.

In the case of an item of equipment comprising a plurality of segments of conductive elastomer, it may be envisaged to fit a plurality of extension members, each positionable on a segment of elastomer, in order to monitor a plurality of arteries. For example, an item of equipment according to the invention, which comprises two segments of elastomer each covering the entire periphery of a wrist may comprise an extension member positionable on each segment. During use, a first extension member would be positioned between the first elastomer segment and the skin at the level of the radial artery, a second extension member would be positioned between the second elastomer segment and the skin at the level of the ulnar artery. The equipment can thus measure with great precision the information relating to these two arteries. Further segments with extension member may be added, to measure for example venous flows.

The equipment according to the invention thus comprises at least one extension member positionable between a segment of conductive elastomer of the equipment and the periphery of the body element to be monitored, at the level of a point of interest which is preferably a channel through which a blood flow travels.

It may be envisaged to use this extension member to make other measurements by integrating therein a miniaturised additional measuring instrument. For example, associating with the extension member a sonic or ultrasonic microphone may make it possible to make Doppler type measurements on the arterial flow, in parallel with the plethysmographic measurement. The result of this measurement could be combined with the other information generated by the equipment of the invention, so as to enhance the precision, quality and range thereof.

Figure 16:
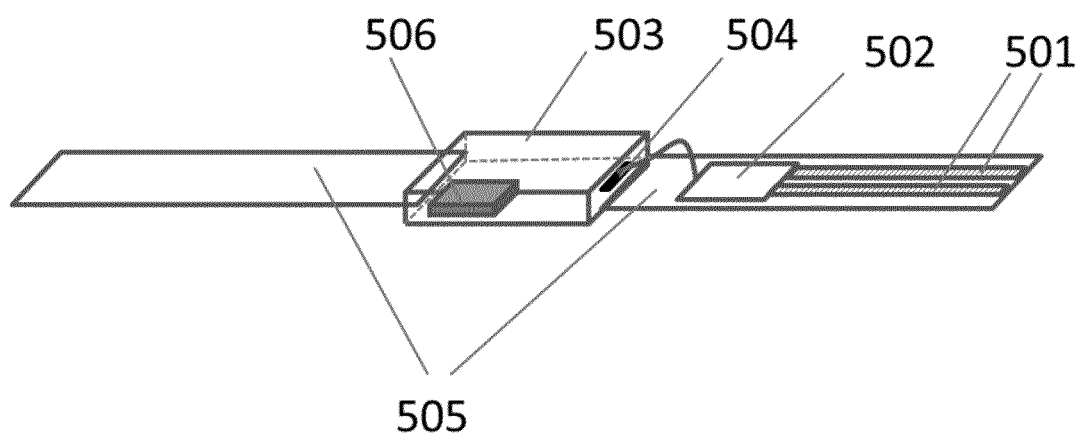
FIG. 16 illustrates schematically the equipment of the invention integrated in the bracelet of a smart watch.

It was mentioned above that the signal data processing system may be, inter alia, a smart watch. With reference to FIG. 16, a smart watch 503 is equipped with a connection port 504, at the level of one of the watch bracelet fasteners 506. It may be envisaged to integrate the equipment of the invention, i.e. at least one conductive elastomer segment 501 (herein, two are shown) and a circuit 502 comprising the means for capturing the length of the segments 501, the signal processing means and optionally the battery, in the bracelet 501 of the watch 503. Once the signal has been processed, it may be transmitted, via the connection port 504 of the watch 503 to a software program, or an application, 506 installed on the watch. The smart watch 503, i.e. suitable for communicating via Wi-Fi, Bluetooth, or 3G or 4G for example, may be programmed to automatically notify medical emergency services in the event of the identification of a problem associated with the subject's blood flows or respiratory cycles. This configuration is of particular interest for subjects presenting with a high risk of heart failure, or serious pulmonary problems. The emergency services can not only intervene quickly but, also, adapt their intervention directly by means of the information supplied by the equipment integrated in the patient's watch bracelet.

The bracelet and the equipment of the invention form an assembly suitable for connection, mechanically for one and electronically for the other, with the smart watch.

For uses in wet environments, for example for undersea diving, the watch bracelet supporting the equipment of the invention could be coated with silicone in order to waterproof same.

The term smart watch has been used herein, but this term should be understood as referring to any watch-sized portable monitoring system integrating different technologies such as for example the Apple Watch.

The equipment of the invention may also be used to monitor a baby's breathing and/or cardiac activity. It may even be envisaged for it to be combined with a baby breathing monitor, such as for example a sensor mat to be placed under a mattress. This type of mat suffers from a lack of sensitivity resulting in false alarms. Combining the information recorded by the mat with the information from a bracelet of the invention could advantageously increase the sensitivity of the whole.

The invention claimed is:

1. A wearable medical device for monitoring blood flow through a blood vessel, comprising:
   at least one segment of a conductive elastomer with a variable resistance that varies in response to changes in its length, the at least one segment of the conductive elastomer being configured to elastically change length in response to:
   blood flow through the blood vessel;
   a circuit coupled to the at least one segment of the conductive elastomer and configured to measure a resistance of the at least one segment of the conductive elastomer as its length varies with blood flow through the blood vessel;
   a clamping member for automatically adjusting a length of the at least one segment of the conductive elastomer; and
   a processor in communication with the circuit and the clamping member, the processor being configured to:
   correlate the measured resistance into one or more parameters of the blood flow to be monitored; and
   generate at least one of an audible, visual, and tactile signal to indicate an end of an adjustment operation of the at least one segment of the conductive elastomer by the clamping member.

2. The wearable medical device according to claim 1, wherein the at least one segment of the conductive elastomer is sized and configured to surround at least a portion of the blood vessel.

3. The wearable medical device according to claim 1, wherein the at least one segment of the conductive elastomer is secured to an adhesive.

4. The wearable medical device according to claim 1, wherein the circuit is a Wheatstone bridge.

5. The wearable medical device according to claim 4, wherein the Wheatstone bridge is connected to a wireless transmitter.

6. The wearable medical device according to claim 5, wherein the wireless transmitter is connected to a wireless receiver of the processor.

7. The wearable medical device according to claim 1, comprising a plurality of segments of conductive elastomer.

8. The wearable medical device according to claim 7, wherein the circuit includes at least two Wheatstone bridges each Wheatstone bridge including a segment of the plurality of segments of the conductive elastomer.

9. The wearable medical device according to claim 1, wherein the clamping member comprises a motor controlled by processor to adjust the length of the at least one segment of the conductive elastomer.

10. The wearable medical device according to claim 1, wherein the at least one segment of the conductive elastomer is a multilayer segment having an alternation of layers of conductive elastomer with layers of non-conductive elastomer.

11. The wearable medical device according to claim 1, further including a rigid atraumatic conductive element coupled to the conductive elastomer, the rigid atraumatic conductive element being configured to be in direct contact with skin of a patient proximate the blood vessel and disposed between the conductive elastomer and the skin.

12. The wearable medical device according to claim 11, wherein the rigid atraumatic conductive element is a bead.

13. The wearable medical device according to claim 1, wherein the at least one segment of the conductive elastomer includes a plurality of conductive sections separated by at least one non-conductive section.

* * * * *